United States Patent [19]

Anderson et al.

[11] Patent Number: 4,588,718
[45] Date of Patent: May 13, 1986

[54] CARBOXY CONTAINING ESTER PRODRUGS OF CORTICOSTEROIDS

[75] Inventors: Bradley D. Anderson, Salt Lake City, Utah; Robert A. Conradi, Portage, Mich.

[73] Assignee: The Upjohn Company, Kalamazoo, Mich.

[21] Appl. No.: 594,098

[22] Filed: Mar. 28, 1984

[51] Int. Cl.$^4$ .............................................. C07J 5/00
[52] U.S. Cl. .................................. 514/172; 514/179; 514/180; 260/239.55 D; 260/397.45
[58] Field of Search ...................... 260/397.45, 397.47, 260/239.55 D; 514/172, 179

[56] References Cited

U.S. PATENT DOCUMENTS

| | | | |
|---|---|---|---|
| 3,415,817 | 12/1968 | Philippson et al. | 260/239.5 |
| 3,471,477 | 10/1969 | Fried | 260/239.5 |
| 3,546,215 | 12/1970 | Fried | 260/239.55 |
| 3,626,063 | 12/1971 | Lincoln et al. | 424/243 |
| 4,296,109 | 10/1981 | Laurent et al. | 424/241 |
| 4,381,307 | 4/1983 | Sloan | 260/397.45 |
| 4,472,392 | 9/1984 | Anderson et al. | 260/397.45 |

FOREIGN PATENT DOCUMENTS

| | | | |
|---|---|---|---|
| 2753838 | 7/1979 | Fed. Rep. of Germany | 260/239.5 |
| 1602266 | 11/1981 | Fed. Rep. of Germany | 260/239.5 |
| 1426922 | 7/1964 | France | 260/239.5 |
| 940701 | 10/1963 | United Kingdom | 260/239.5 |
| 1375357 | 11/1974 | United Kingdom | 424/241 |

OTHER PUBLICATIONS

Anderson, B. D., et al., "Influence of Premicellar and Micellar Association on the Reactivity of Methylprednisolone 21-Hemiesters in Aqueous Solution," J. Pharm. Sci. 72(4), Apr. 1983, pp. 448-454.
Anderson, B. D. and Taphouse, V., "Initial Rate Studies of Hydrolysis and Acyl Migration in Methyl prednisolone 21-Hemisuccinate and 17-Hemisuccinate," J. Pharm. Sci. 70(2), Feb. 1981, pp. 181-186.
Flynn, G. L. and Lamb. D. J., "Factors Influencing Solvolysis of Corticosteroid-21-phosphate Esters, J. Pharm. Sci. 59(10), Oct. 1970, pp. 1433-1438.
Garrett, E. R., "Prediction of Stability in Pharmaceutical Preparations X: Alkaline Hydrolysis of Hydrocortisone Hemmisuccinate," J. Pharm. Sci. 51(5), May 1962, pp. 445-450.
Garrett, E. R., "The Solvolysis of 21-Hydrocortisone Esters and Hemiesters," J. Med. Pharm. Chem. 5, 1962, pp. 112-133.
Kawamura, M., et al., "Pharmaceutical Studies on Water-soluble Corticosteroid Derivatives III. Stability of Hydrocortisone-21-Sulfobenzoates and 21-Sulfate in Solution," Yakugaku Zasshi 91, 1971, pp. 871-878.
Kawamura, M., et al., "Pharmaceutical Studies on Water-soluble Corticosteroid Derivatives. II. Stability of Hydrocortisone 21-Aminoalkylcarboxylates in Solution," Yakugaku Zasshi 91, 1971, pp. 863-870.
Yamamoto, R., et al., "Pharmaceutical Studies on Water-soluble Corticosteroid Derivaties. I. Stability of Hydrocortisone 21-Hemiesters in Solution," Yakugaku Zasshi 91, 1971, pp. 855-862.

Primary Examiner—Elbert L. Roberts
Attorney, Agent, or Firm—L. Ruth Hattan

[57] ABSTRACT

A compound of the formula

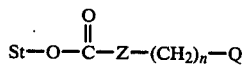

wherein
St represents a corticosteroid moiety bonded to the carbonyl via the
21-hydroxy group of said corticosteroid;
wherein
Z is a bond or —O—;
wherein
n is an integer from 4 to 9;
wherein
Q is
(1) Y—$CH_2$COOH wherein Y is —S—, —S(O)—, —S($O_2$)—, —$SO_2$N(R)—, or —N(R)$SO_2$; R is hydrogen or lower alkyl($C_1$-$C_4$) with the proviso that the total carbon atoms in R and $(CH_2)_n$ is not greater than 10;
(2)

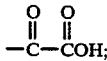

or
(3)

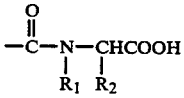

wherein
$R_1$ is hydrogen and $R_2$ is H, $CH_3$, $CH_2COOH$, $CH_2CH_2COOH$, $CH_2OH$, $CH_2SH$, $CH_2CH_2SCH_3$, or $CH_2Ph$—(OH) wherein Ph is phenyl and Ph—(OH) is p-hydroxyphenyl; or $R_1$ is $CH_3$ and $R_2$ is H; or $R_1$ and $R_2$ taken together are —$CH_2CH_2CH_2$—; or N($R_1$)CH($R_2$) COOH taken together is NH$CH_2$CONH$CH_2$COOH; and pharmaceutically salts thereof.

12 Claims, No Drawings

CARBOXY CONTAINING ESTER PRODRUGS OF CORTICOSTEROIDS

BACKGROUND OF THE INVENTION

Conventional anti-inflammatory steroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. The term "prodrug" denotes a derivative of an active drug which is converted after administration back to the active drug. The "pro-moiety" referred to in this application is the fragment attached to the steroid via an ester linkage and removed by ester hydrolysis in vivo. A major problem with many common derivatives is their solution instability. Dicarboxylic acid hemiesters of corticosteroids such as succinate esters, for example, are marketed commercially as lyophilized powders for reconstitution prior to injection due to their solution instability (see, for example, E. R. Garrett, J. Pharm. Sci., 51, 445 (1962) and J. Med. Pharm. Chem. 5, 112 (1962); B. D. Anderson and V. Taphouse, J. Pharm. Sci., 70, (1981); R. Yamamoto, S. Fujisawa, and M. Kawamura, Yakugaku Zasshi, 91, 855 (1971); B. D. Anderson, et al., J. Pharm. Sci. 72, 448 (1983)). Corticosteroid 21-aminoalkyl carboxylate derivatives reported in the literature also undergo rapid hydrolysis in aqueous solution (M. Kawamura, R. Yamamoto, and S. Fujisawa, Yakugaku Zasshi, 91, 863 (1971)).

Certain derivatives which do appear to exhibit better solution stability suffer from other disadvantages. 21-sulfate esters, for example, may not be readily converted to the active parent drug in vivo as suggested by the fact that the 21-sulfate of hydrocortisone is inactive in mice (M. Kawamura, R. Yamamoto, and S. Fujisawa, Yakugaku Zasshi, 91, 871 (1971); meta-sulfobenzoate esters which have been reported as having improved solution stability (M. Kawamura, R. Yamamoto and S. Fujisawa, ibid, French Patent Derwent No. 76199 U)) are frequently not highly water soluble and thus may have limited utility as injectable prodrugs. Phosphate esters may in some cases possess the requisite solubility, solution stability, and bioconversion rates but exhibit other disadvantages. Several undesirable features of phosphate esters are apparent: (1) Phosphate esters are often difficult to purify and are frequently very hygroscopic. (2) The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid due to micelle formation by the intact prodrug is a desirable feature which phosphate esters exhibit to only a limited extent. (4) Concentrated solutions of phosphate esters of corticosteroids exhibit accelerated reaction velocities due to micelle formation, limiting shelf-life in concentrated solutions (G. L. Flynn and D. J. Lamb, J. Pharm. Sci., 59, 1433 (1970)). Sulfopropionate esters of corticosteroids have also been reported as readily water soluble and as having improved solution stability (Derwent Accession No. 27789 C). Sulfoacetate esters are also known (Derwent 9453F). The present invention provides a class of novel compounds which are solution stable prodrugs of corticosteroids.

FIELD OF INVENTION

The present invention is novel carboxy containing ester prodrugs of corticosteroids and formulations of steroid prodrugs.

SUMMARY OF INVENTION

The compounds of the present invention are carboxy containing ester prodrugs of corticosteroids which are solution stable in vitro but are rapidly converted in vivo to the active parent drug and are therefore useful as anti-inflammatory agents. The compounds of the present invention are represented by the following general Formula I:

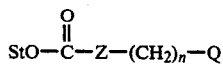

Formula I wherein
St represents a corticosteroid moiety bonded to the carbonyl via the 21-hydroxy group of said corticosteroid; Z is a bond, or —O—; and n is an integer of from 4 to 9; Q is
(1) Y—$CH_2$COOH wherein Y is —S—, —S(O)—, —S($O_2$)—, —$SO_2$N(R)—, or —N(R)$SO_2$; R is hydrogen or lower alkyl($C_1$-$C_4$) with the proviso that the total carbon atoms in R and ($CH_2$)$_n$ is not greater than 10;

(2)

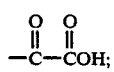

(3)

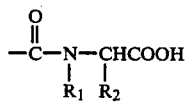

wherein
$R_1$ is hydrogen and $R_2$ is H, $CH_3$, $CH_2$COOH, $CH_2CH_2$COOH, $CH_2$OH, $CH_2$SH, $CH_2CH_2SCH_3$, or $CH_2$Ph—(OH) wherein Ph—(OH) is p-hydroxyphenyl; or $R_1$ is $CH_3$ and $R_2$ is H; or $R_1$ and $R_2$ taken together are —$CH_2CH_2CH_2$—; or N($R_1$)CH($R_2$)COOH taken together is NH$CH_2$CONH$CH_2$COOH.

Pharmaceutically acceptable base addition salts of the compounds of Formula I are also a part of the present invention. Any reference herein to the compounds of Formula I is intended to include pharmaceutically acceptable salts thereof. Solution stable formulations of the compounds of Formula I are also a part of the present invention.

DETAILED DESCRIPTION OF INVENTION

In the compounds of general Formula I St represents the parent corticosteroid minus the 21-hydroxyl group of said corticosteroid which is necessary to form the novel esters of the present invention. The parent corticosteroid could be depicted as StOH wherein the OH is located at the 21-position of the corticosteroid which may be depicted as follows:

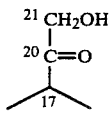

Of course the carbon atoms at positions C-17 and C-21 may be substituted as will be apparent from the description hereinbelow.

The term corticosteroid as used herein is taken to mean not only the steroids produced by the adrenal cortex but also synthetic equivalents, i.e., non-naturally occurring steroids which possess physiological properties characteristic of naturally occurring corticosteroids. Reference is made to *Drill's Pharmacology in Medicine*, McGraw-Hill Book Company, New York, (1965), Chapter 73: Adrenal Cortex and Adrenocortical Hormones, particularly pages 1185-1187 wherein typical corticosteroids employed in the present invention are described. Also, typical corticosteroids represented by StOH include those described in Applezweig, *Steroid Drugs*, McGraw-Hill Book Company, Inc., New York, 1962, pp. 435-731, and in particular the compounds associated with the following parenthetical numbers:

675; 684; 685; 734; 1030; 1033; 1034; 1035; 1036; 1038; 1039; 1048; 1051; 1052; 1059; 1061; 1063; 1064; 1066; 1067; 1068; 1070; 1071; 1072; 1073; 1078; 1080; 1082; 1083; 1084; 1086; 1087; 1088; 1092; 1093; 1094; 1095; 1099; 1100; 1101; 1105; 1107; 1108; 1109; 1110; 1111; 1112; 1116; 1116-A; 1117; 1119; 1120; 1121; 1125; 1128; 1135; 1140; 1141; 1142; 1143; 1149; 1151; 1155; 1168; 1169; 1170; 1172; 1173; 1174; 1175; 1176; 1178; 1181; 1182; 1182-A; 1183; 1184; 1186; 1187; 1189; 1193; 1194; 1197; 1198; 1206; 1207; 1214; 1215; 1216; 1217; 1218; 1220; 1221; 1226; 1227; 1230; 1231; 1242; 1243; 1244; 1246; 1248; 1251; 1270; 1272; 1273; 1274; 1275; 1279; 1280; 1281; 1282; 1283; 1285; 1286; 1287; 1294; 1295; 1296; 1306; 1307; 1308; 1319; 1320; 1322; 1323; 1324; 1325; 1327; 1328; 1329; 1330; 1331; 1333; 1334; 1336; 1337; 1338; 1339; 1340; 1350; 1351; 1352; 1363; 1368; 1370; 1385.

Also, typical corticosteroids represented by StOH include those described in Applezweig, *Steroid Drugs*, Holden-Day, Inc., San Francisco, 1964, pp. 109-438, and in particular the compounds associated with the following "catalogue" numbers:

2680; 2681; 2709; 2713; 2714; 2716; 2717; 2719; 2720; 2722; 2723; 2724; 2725; 2726; 2727; 2728; 2729; 2730; 2731; 2732; 2733; 2734; 2735; 2746; 2737; 2738; 2739; 2740; 2741; 2742; 2743; 2744; 2745; 2746; 2814; 2826; 2827; 3036-A; 3036-B; 3036-C; 3036-D; 3036-E; 3036-F; 3036-G; 3036-H; 3036-I; 3036-J; 3036-K; 3036-L; 3036-M; 3036-N; 3036-O; 3036-P; 3036-Q; 3036-R; 3036-S; 3036-T; 3036-U; 3036-V; 3052; 3054; 3057; 3071; 3073; 3074; 3075; 3078; 3081; 3082; 3087; 3088; 3090; 3108; 3109; 3109-A; 3111; 3112; 3112-A; 3114; 3117; 3118; 3119; 3119A; 3120; 3121; 3122; 3122-A; 3123; 3124; 3130; 3131; 3132; 3133; 3139; 3140; 3141; 3142; 3143; 3143-A; 3145; 3147; 3148; 3151; 3152; 3154; 3168; 3169; 3170; 3171; 3171-A; 3174; 3175; 3175-A; 3178; 3180; 3181; 3182; 3183; 3184; 3184-A; 3189; 3191; 3192; 3193; 3193-A; 3196; 3198; 3199; 3200; 3201; 3202; 3203; 3204; 3205; 3206; 3215; 3216; 3217; 3218; 3220; 3222; 3226; 3227; 3231; 3232; 3232-A; 3234; 3235; 3235-A; 3237; 3238; 3239; 3240; 3241; 3242; 3242-A; 3248; 3249; 3250; 3251; 3251-A; 3253; 3254; 3255; 3256; 3257; 3258; 3259; 3260; 3265; 3266; 3267; 3268; 3269; 3273; 3287; 3288; 3289; 3289-A; 3291; 3292; 3293; 3293-A; 3296; 3297; 3298; 3299; 3300; 3301; 3302; 3303; 3303-A; 3316; 3317; 3318; 3319; 3319-A; 3332; 3333; 3334; 3335; 3337; 3338; 3339; 3340; 3341; 3342; 3343; 3344; 3345; 3346; 3347; 3349; 3350; 3351; 3372; 3373; 3373-B; 3374; 3375; 3376; 3377; 3379.

The corticosteroid field, i.e., the compounds and their use as pharmacologically active agents is well documented, and numerous other references exist which describe the synthesis and use of corticosteroids as depicted above by StOH. Substantially any corticosteroid having a hydroxyl group at the C-21 position of the molecule is useful as the parent steroid in forming the novel esters of the present invention. The compounds of Formulas A and B (see Formula Chart) represent preferred corticosteroids used to contribute the St moiety of the compounds of Formula I. Particularly preferred corticosteroids which are useful in forming the esters of Formula I are the following: hydrocortisone, cortisone, corticosterone, prednisone, prednisolone, 6α-methylprednisolone, triamcinolone, dexamethasone, betamethasone, flumethasone, 11-deoxy corticosterone, fluprednisolone, 9α-fluorohydrocortisone, flurandrenolone, paramethasone, chlorprednisone, and dehydrocorticosterone. The compounds of Formula I wherein Z is a bond are more preferred. Also compounds of Formula I wherein Q is Y—CH$_2$COOM or

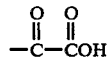

are preferred.

Illustrative examples of pharmaceutically acceptable base addition salts of the compounds of Formula I are alkali metal salts or organic tertiary amine salts as formed by treatment with a suitable base as set forth hereinbelow.

The compounds of Formula I are prodrugs of the corticosteroids represented by the St moiety in said Formula and have the same utility as the known or parent corticosteroid. Thus the compounds of Formula I are useful in treating warm blooded animals, e.g., dogs, cats, monkeys, horses, and particularly humans for various disease conditions. For example, the compounds of Formula I are useful in those situations where one wishes to elicit an anti-inflammatory, anti-pruritic or vasoconstrictive action inherent in the parent corticosteroid. The compounds of the present invention and the compounds utilized in the novel formulations of the present invention are particularly useful in treating acute adrenal insufficiency (Addison's disease); allergic conditions such as asthma, contact dermatitis, serum sickness, angioneurotic edema, drug hypersensitivity reactions and anaphylactoid reactions; collagen and musculoskeletal diseases, such as, rheumatoid arthritis; dermatomyositis, lupus erythematosus, rheumatic fever; dermatological diseases, such as, pemphigus and severe erythema multiforme; ulcerative colitis, and acute exacerbations of multiple sclerosis. Also when the parent corticosteroid contributing the St moiety of the compounds of Formula I possesses mineralocorticoid properties said compounds of Formula I are useful particularly in maintaining a physiological electrolyte level in patients with acute adrenal insufficiency.

Although the compounds of Formula I and salts thereof may be administered orally, these compounds are designed for and have their primary application in those situations where oral therapy is not feasible. The compounds of Formula I are best suited for administration as sterile aqueous solutions by intravenous injection, intravenous infusion, or intramuscular or subcutaneous injection, or intravenous bolus.

The novel compounds of the present invention provide marked advantages over known corticosteroids or derivatives thereof in that these novel compounds are highly water soluble and when formulated in a manner which fully exploits the advantageous physicochemical properties of these compounds are sufficiently stable in aqueous solution to afford long term storage of solutions of said novel compounds.

The solution stability of these compounds is due to several features: (1) The derivatives have terminal carboxyl groups with lowered pKa's such that these compounds become highly soluble at or closer to the pH range in which ester hydrolysis in aqueous solution is minimized. (2) Functional groups which may promote ester hydrolysis through any catalytic or substituent effect are sufficiently distant from the ester linkage that such influences are minimized. (3) The compounds self-associate in concentrated solutions to form molecular aggregates which increase the shelf life of formulations by (a) retarding hydroxide ion catalyzed ester hydrolysis at high concentrations, and (b) solubilizing any parent corticosteroid present in and resulting from the hydrolysis of a solution of a compound of the present invention.

Physical-Chemical Data

The compounds of this invention tend to be free flowing non-hygroscopic crystalline solids when in the acid form. While the aqueous solubility of these prodrugs is limited at very low pH values, these compounds become very soluble at pH values around 5 or higher. In this pH range the prodrugs self-associate to form micellar solutions. The solubility of Example 1 is greater than 160 mg/ml at pH 4.8 and above at room temperature.

The solution stability of the compounds of this invention varies to some extent depending on the nature of the promoiety. For all of the compounds pH is a critical parameter and formulations of the prodrugs must be buffered at the optimal pH to fully take advantage of the inherent stability of the compounds. The temperature of storage is also critical to the stability of these compounds; thus refrigerated storage can greatly enhance formulation shelf-lives. Finally, the concentration of the prodrug in solution influences both the pH of maximum stability and the degree of stability that is attainable. This is a consequence of the tendency of these compounds to self-associate into micelle-like aggregates.

The most important reaction affecting shelf-life is hydrolysis of the ester or carbonate linkage. From the hydrolysis rate constants determined at 25° C. at various pH values for dilute aqueous solutions of the compounds of this invention, estimates of $t_{90\%}$ (time for 10% hydrolysis) may be calculated. Such values, calculated at the pH of optimum stability, for the compounds of Examples 1 and 2 are listed in Table I.

TABLE I

| Compound | pH | $t_{90\%}$ (years) |
|---|---|---|
| Example 1 | 4.7 | 2.0 |
| Example 2 | 4.6 | 0.93 |

The actual shelf-life of formulations of the above compounds would be expected to differ from the above estimates for several reasons. (1) The solubility of the parent corticosteroid formed on hydrolysis may be exceeded prior to 10% degradation of the ester. Micelle formation by the intact prodrugs results in solubilization of free corticosteroid thereby prolonging shelf-life. The degree of solubilization varies with the ester concentration, nature of the pro-moiety, and the structure of the corticosteroid. (2) Other degradation reactions besides hydrolysis may be expected to occur. These should in general be diminished due to micelle formation and can in some cases be controlled by the addition of chelating agents, antioxidants, etc. (3) Micelle formation in concentrated solutions also results in stabilization of the ester linkage toward base catalyzed hydrolysis. For example, the base catalyzed hydrolysis rate constant in a 0.267M solution of the compound of Example 1 is less than 20% the rate constant in a $5 \times 10^{-4}$M solution. Although acid catalyzed hydrolysis is generally accelerated in concentrated solutions, thus making the compounds somewhat less stable at low pH values, this destabilization is more than offset by the enhanced base stability.

Formulations of the compounds of this invention would be prepared by dissolving an appropriate amount of the acid prodrug in aqueous solution using a pharmaceutically acceptable base to convert the prodrug to its salt form. Alternatively the prodrugs would be initially prepared as salts and then dissolved in aqueous solutions. Suitable agents for preparing these salts would be inorganic bases such as NaOH, KOH and MgOH or organic bases such as choline (OH$^-$), tris-hydroxymethylmethylamine, triethanolamine, etc.

In addition to prodrug and the cation used to make the salt form, a suitable buffer must also be included to maintain optimal pH in the formulations. This pH varies with structure but generally is in the range of 3–6. Suitable buffers include acetate, succinate, adipate and citrate. The quantity of buffer used is determined by means known in the art and will depend on the pH desired, the concentration of the solution, and the buffering capacity of the buffer. Preservatives such as benzyl alcohol, parabens, sorbic acid, or phenol may be added if a multiple dose formulation is desired. Chelating agents such as citric acid or ethylenediaminetetraacetic acid (EDTA) and antioxidants such as sodium bisulfite, ascorbic acid or tocopherol may also be included in formulations. Finally other stabilizing agents such as creatinine, niacinamide or polysorbate 80 may be included in formulations of the prodrugs.

The concentration of the solution stable formulations of the compounds of Formula I depends on the activity level of and the ultimate dose of parent corticosteroid desired. In general the stability of the formulations increases as the concentration of novel ester increases. In essence the solution stable formulations may be as concentrated as viscosity properties permit or until the solubility of the novel ester is exceeded. Inasmuch as the compounds of the present invention are converted to the parent corticosteroid in vivo, ideally the concentration of the novel ester and the volume of the solution administered will be chosen to provide a quantity of parent corticosteroid which is known to be effective. For example, a 0.267M solution of the compound in Example 1, set forth below, is equivalent to 100 mg/ml of 6α-methylprednisolone.

Typical formulations useful in practicing the present invention are set forth below.

Since the compounds of Formula I are prodrugs of the parent corticosteroids, their efficacy depends on bioconversion to liberate the free corticoid in vivo. To demonstrate the bioconversion of the compounds of Formulas I and II to the parent steroid in vivo the following experiment was performed. Four female monkeys having synchronized menstrual cycles were given on separate days three days apart doses of the compound of Examples 1 and 2 and methylprednisolone hemisuccinate equivalent to 7.5 mg/kg. Prior to dosing the monkeys were fasted overnight and each was anesthetized during dosing. A few mls of 0.01μ ion strength pH 5 sodium acetate buffer was added to the test compound and 1N sodium hydroxide was added slowly with rapid stirring until all the solids went into solution just prior to injection. Blood samples were withdrawn at times 0, 1/12, ¼, 1, 2, 4 and 8 hours from administration of test compound and levels of test compound and parent steroid were measured. The compounds of Examples 1 and 2 were shown to be converted to the parent steroid, ie, methylprednisolone to at least the same extent as was methylprednisolone hemisuccinate.

The compounds of Formula I wherein Z is a bond, Q is $-Y-CH_2COOH$ and Y is $-S-$, $-S(O)-$ or $-S(O)_2-$ are prepared by reacting a corticosteroid of the formula St—X  Formula II wherein St has the meaning defined in Formula I and X is $-OSO_2CH_3$ or iodo, with a molar excess of a compound of Formula III HOOC(CH$_2$)$_n$—Y'—CH$_2$COOH  Formula III wherein Y' is S, S(O), or S(O)$_2$ and n is an integer from 4 to 9. The reaction is carried out in a polar aprotic solvent such as DMF or DMSO in the presence of at least 2 moles of an appropriate base per mole of the compound of Formula III. The most preferred base is a bicyclic amidine such as 1,8-diazabicyclo[5.4.0]undec-7-ene (DBU).

Compounds of Formula III wherein Y is $-SO_2-$ are prepared by treating a compound of Formula IV $$\underset{HOC(CH_2)_mSCH_2COH}{\overset{O\quad\quad O}{\|\quad\quad\|}}$$ Formula IV with an oxidant such as a 1:1 mixture of glacial acetic acid and 30% hydrogen peroxide or potassium hydrogen persulfate in aqueous methanol. Compounds of Formula III wherein Y is $-SO-$ are prepared by treating a compound of Formula IV with an equimolar amount of sodium periodate (NaIO$_4$) in aqueous methanol at 10° to 15° C. for approximately one hour. The reaction should be monitored to prevent over oxidation to the sulfone. Compounds of Formula IV are prepared by reacting one equivalent of a compound of Formula V $$\underset{HOC(CH_2)_mBr}{\overset{O}{\|}}$$ Formula V with one equivalent of mercaptoacetic acid in water in the presence of three equivalents of strong base such as NaOH or KOH.

Compounds of Formula I wherein Z is a bond, Q is Y—CH$_2$COOH and Y is —N(R)SO$_2$— are prepared by treating a compound of Formula VI HOOC(CH$_2$)$_n$N(R)SO$_2$CH$_2$COOH  Formula VI wherein n and R are as defined in Formula I with one equivalent of a compound of Formula II wherein X is iodo in a polar aprotic solvent such as dimethyl formamide, dimethyl sulfoxide or tetrahydrofuran in the presence of at least two equivalents of a bicyclic amidine such as 1,8-diazabicyclo[5.4.0]undec-7-ene (DBU) or a sterically hindered tertiary amine such as diisopropylethylamine. Preferably the reaction is carried out at room temperature using two equivalents of DBU.

Compounds of Formula VI are prepared by treating compounds of Formula VII with aqueous mineral acid.

$$\underset{R_aOC(CH_2)_nN(R)SO_2CH_2COR_a}{\overset{O\quad\quad\quad\quad\quad\quad O}{\|\quad\quad\quad\quad\quad\quad\|}}$$ Formula VII In Formula VII n and R are as defined in Formula I and R$_a$ is a lower alkyl(C$_1$-C$_4$) straight or branched chain. Compounds of Formula VII are prepared by treating an amino acid ester of the formula R$_a$OOC(CH$_2$)$_n$N(R)H wherein R$_a$, n and R are as defined in Formula VII with a sulfonyl chloride of the formula ClSO$_2$CH$_2$COOR$_a$ wherein R$_a$ is as defined in Formula VII in a polar aprotic solvent in the presence of pyridine as a catalyst. The amino ester compounds are prepared by refluxing an amino acid of the formula HOOC(CH$_2$)$_n$N(R)H wherein n and R are as defined in Formula I in an appropriate lower alcohol in the presence of a catalytic amount of sulfuric acid or anhydrous hydrochloric acid. The amino acids are known in the art or are obtained by treating an acid of the formula HOOC(CH$_2$)$_n$X wherein X is Cl, Br, I, O-mesyl or O-tosyl with an amine of the formula RNH$_2$. The sulfonyl chloride compounds are prepared by treating a sulfoacetic ester of the formula HSO$_3$CH$_2$COOR$_a$ wherein R$_a$ is as defined above with thionyl chloride in an aprotic solvent or neat with excess thionyl chloride. Dimethylformamide may be added as a catalyst. The sulfoacetic acids are prepared by esterification of sulfoacetic acid in a refluxing lower alcohol.

The compounds of Formula I wherein Z is a bond, Q is Y—CH$_2$COOH and Y is —SO$_2$N(R)— are prepared by condensing a bis acid of the formula HOOC(CH$_2$)$_n$SO$_2$N(R)CH$_2$COOH  Formula VIII wherein n and R are as defined in Formula I with a compound of Formula II wherein X is iodo in a polar aprotic solvent in the presence of at least two equivalents of DBU or a hindered tertiary amine per equivalent of compound of Formula VIII. The compounds of Formula VIII are prepared by acid or base hydrolysis of the corresponding bis ester, i.e., a compound of formula $R_aOOC(CH_2)_nSO_2N(R)CH_2COOR_a$ wherein R, n and $R_a$ are as defined hereinabove, and the bis ester is obtained by condensing an amine ester of the formula $H(R)NCH_2COOR_a$ with a sulfonyl chloride compound of the formula $R_aOOC(CH_2)_nSO_2Cl$ in a polar aprotic solvent such as dimethyl formamide, tetrahydrofuran or dimethylsulfoxide in the presence of pyridine as a catalyst. The sulfonyl chloride is obtained by treating an acid of the formula $HOOC(CH_2)_nR_b$ wherein $R_b$ is, e.g., Cl, Br, I, O-mesyl or O-tosyl with sodium sulfite in aqueous methanol or ethanol at reflux to give the sulfonic acid $HOOC(CH_2)_nSO_3H$ which is further refluxed in an anhydrous lower alcohol to give the carboxy ester derivative which is treated with excess thionyl chloride in the presence of a catalytic amount of dimethyl formamide.

Compounds of Formula I wherein Z is —O—, Q is $YCH_2COOH$ and Y is S, S(O) or $S(O)_2$ are prepared by reacting a corticosteroid StOH wherein St is as defined in Formula I with a compound of Formula IX

$R_cOCOO(CH_2)_n—Y'—CH_2COOCH_3$   Formula IX wherein $R_c$ is p-nitrophenyl, Y' is S, S(O) or $S(O)_2$ and n is an integer of from 4 to 9 in a polar aprotic solvent such as tetrahydrofuran, dimethylformamide or dimethylsulfoxide in the presence of an acylation catalyst such as dimethylaminopyridine (DMAP) or N-methylimidazole and subsequently acid hydrolyzing the resulting ester to the corresponding acid. The Formula IX compounds are prepared by treating an ester alcohol of the Formula $HO(CH_2)_n—Y'—CH_2COOCH_3$ wherein Y' and n are as defined above with equimolar amounts of p-nitrophenyl chlorocarbonate and a tertiary amine, e.g., triethylamine or pyridine in an aprotic solvent such as acetone, chloroform or tetrahydrofuran. The ester alcohols wherein Y' is —S— are obtained by reacting one equivalent of a compound of the formula $HO(CH_2)_nR_b$ wherein n is 4 to 9 and $R_b$ is Cl, Br, I, O-mesyl or O-tosyl with one equivalent of mercaptoacetic acid in water in the presence of sodium hydroxide or potassium hydroxide. The thus obtained compounds of the formula $HO(CH_2)_n—S—CH_2COOCH_3$ can be oxidized to the sulfone by treatment with an equimolar amount of $NaIO_4$ in an aqueous alcohol at 0° to 10° C. or to the sulfoxide by treatment with potassium hydrogen persulfate in aqueous alcohol. These oxidation steps may convert the carboxy methyl ester to the free acid and thus the resulting sulfone and sulfoxide can be reesterified, e.g., by treatment with a catalytic amount of a strong acid such as sulfuric acid or toluenesulfonic acid in methanol.

The compounds of Formula I wherein Z is —O—, Q is —Y—$CH_2COOH$, and Y is —$SO_2N(R)$— are prepared by treating a compound of Formula X

$R_cOCOO(CH_2)_nSO_2N(R)CH_2COOCH_3$   Formula X wherein R and n are as defined in Formula I and $R_c$ is p-nitrophenyl with a corticosteroid of the formula StOH wherein St is as defined in Formula I in a polar aprotic solvent such as dimethylformamide, tetrahydrofuran, or dimethylsulfoxide in the presence of one equivalent of a tertiary amine such as pyridine or triethylamine and a catalytic amount of an acylation catalyst such as dimethylaminopyridine or N-methylimidazole and selectively hydrolyzing the resulting ester to the acid by treating the ester with an aqueous solution of a strong acid such as hydrochloric or sulfuric. The Formula X compounds are prepared by treating a sulfonyl chloride of the formula $R_cOCOO(CH_2)_nSO_2Cl$ wherein n and $R_c$ are as defined above with two equivalents of the methyl ester of glycine or N-alkyl($C_1$-$C_4$) glycine in a suitable aprotic solvent such as tetrahydrofuran, dimethylformamide or dioxane. The sulfonyl chlorides are obtained by reacting an alcohol of the formula $HO(CH_2)_nR_b$ wherein n and $R_b$ are as defined hereinabove with a sulfite salt such as sodium sulfite in an aqueous lower alkanol at reflux to give compounds of the formula $HO(CH_2)_nSO_3^-$ which are reacted with p-nitrophenylchloroformate in a dry polar aprotic solvent such as dimethylformamide or dimethylsulfoxide in the presence of a tertiary amine such as triethylamine or pyridine at 0° to 20° C. to give compounds of the formula $R_cOCOO(CH_2)_nSO_3$—$R_d$ wherein $R_c$ is p-nitrophenyl, n is 2–9, and $R_d$ is a trialkyl($C_1$-$C_4$) ammonium or pyridinium which are treated with thionyl chloride either using excess thionyl chloride as solvent or using an aprotic solvent such as dimethylformamide.

The compounds of Formula I wherein Z is —O—, Q is $YCH_2COOH$ and Y is —$N(R)SO_2$— are prepared by treating a steroid of the formula StOH wherein St has the meaning defined in Formula I with a compound of Formula XI

$R_cOCOO(CH_2)_nN(R)SO_2CH_2COOCH_3$   Formula XI wherein n and R are as defined in Formula I and $R_c$ is p-nitrophenyl in a dry polar solvent such as dimethyl formamide or dimethylsulfoxide in the presence of an acylation catalyst such as DMAP or N-methylimidazole. The reaction will proceed at room temperature but is preferably carried out at about 40° to 50° C. The resulting ester is then selectively hydrolyzed with an aqueous acid such as hydrochloric, sulfuric or methanesulfonic. The Formula XI compounds are prepared by reacting p-nitrochloroformate with an alcohol ester of the formula $HO(CH_2)_nN(R)SO_2CH_2COOCH_3$ in a dry polar aprotic solvent in the presence of a tertiary amine. The alcohol esters are obtained by reacting a sulfonyl chloride of the formula $ClSO_2CH_2COOCH_3$ with an amino alcohol of the formula $HO(CH_2)_nNH(R)$ in an aprotic solvent and a stoichiometric amount of a tertiary amine. The amino alcohols are commercially available or prepared by reacting a primary amine with a halo alcohol, $HO(CH_2)halo$, and the sulfonyl chloride is prepared by well known procedures.

The compounds of Formula I wherein Z is a bond and Q is

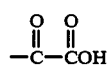

$$\begin{array}{c} O \quad O \\ \parallel \quad \parallel \\ -C-COH \end{array}$$

are prepared by treating a steroid of the Formula II wherein X is iodo with a slight molar excess of a compound of the formula $HOCO(CH_2)_nCOCOOH$ (Formula XII) in a polar aprotic solvent such as dimethylformamide or dimethylsulfoxide at room temperature in the presence of two molar equivalents of an organic base such as a tertiary amine but more preferably a bicyclic amidine such as DBU. The Formula XII compounds are obtained by treating appropriate diesters of dicarboxylic acids with one equivalent of diethyl oxylate in the presence of one equivalent of sodium ethoxide in ethanol, or preferably in an aprotic solvent such as diethyl ether to give after aqueous workup intermediate triesters of the formula

```
alkyl-OCO(CH2)n−1—CHCOO—alkyl
                  |
                  COCOO—alkyl,
``` wherein alkyl has 1 to 4 carbon atoms which are then treated with 4N HCl at 60°–70° for 5–10 hours to give the α-keto-dicarboxylic acids.

The compounds of Formula I wherein Z is —O— and Q is

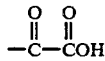

$$-\overset{O}{\underset{\|}{C}}-\overset{O}{\underset{\|}{C}}OH$$

are prepared by treating a steroid of the formula StOH wherein St is as defined in Formula I with a small molar excess of a compound of the formula R$_c$OCOO(CH$_2$)$_n$COCOOCH$_3$     Formula XIII wherein n is as defined in Formula I and R$_c$ is p-nitrophenyl in a polar aprotic solvent at 40° to 50° C. in the presence of one equivalent of organic base such as DMAP or a mixture of DMAP and pyridine and selectively hydrolyzing the resulting ester with aqueous acid. The compounds of Formula XIII are prepared by treating compounds of the formula HO(CH$_2$)$_n$COCOOH (Formula XIV) with two equivalents each of triethylamine and p-nitrophenylchlorocarbonate in a suitable solvent such as tetrahydrofuran at 0° C. for 20 minutes then adding excess methanol and one additional equivalent of triethylamine and allowing the mixture to warm to room temperature. The compounds of Formula XIV are obtained by treating a lactone of the formula

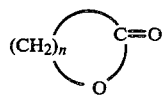

Formula XV with aqueous potassium hydroxide and treating the resulting potassium alkanoate salt with iodoacetamide to give compounds of the formula HO(CH$_2$)$_n$COOCH$_2$CONH$_2$ which are treated with a stoichiometric amount of chlorotriphenylmethane in dry pyridine at 100° C. for one hour to give compounds of the formula R$_e$O(CH$_2$)$_n$COOCH$_2$CONH$_2$ wherein n is 2 to 8 and R$_e$ is triphenylmethyl. The triphenylmethyl derivatives are treated with aqueous base to give R$_e$O(CH$_2$)$_n$COOH which compounds are treated with excess thionyl chloride then heated at 150° to 200° C. for about two hours in the presence of excess cuprous cyanide to give R$_e$O(CH$_2$)$_n$COCN which compounds are treated with concentrated HCl for several days to give HO(CH$_2$)$_n$COCOOH compounds.

The compounds of Formula I wherein Z is a bond and Q is —CON(R$_1$)CH(R$_2$)COOH are prepared by activating the carboxylic acid of a compound of the formula StO—C(=O)—(CH$_2$)$_n$COOH (Formula XVII) by treatment with stoichiometric amounts of isobutylchloroformate and triethylamine in a dry aprotic solvent at −10° to 0° C. for 15 to 20 minutes then adding an appropriate amino acid along with one equivalent of pyridine or triethylamine. Appropriate amino acids for this reaction and the one described below are glycine, sarcosine, alanine, aspartic acid, proline, glutamic acid, serine, threonine, cysteine, methionine, tyrosine, or glycylglycine. The compounds of Formula XVII are prepared by treating a compound of Formula II, i.e., StX, with a stoichiometric amount of a sterically hindered tertiary amine such as diisopropylethylamine and a large excess of a dicarboxylic acid of the formula HOOC(CH$_2$)$_n$COOH in a polar aprotic solvent. When X in Formula II is iodo the reaction is carried out at room temperature and when X is O-mesyl the reaction is carried out at about 45° to 60° C.

The compounds of Formula I wherein Z is —O— and Q is —CON(R$_1$)CH—(R$_2$)COOH are prepared by treating a steroid StOH wherein St has the meaning defined in Formula I with a compound of the Formula R$_c$OCOO(CH$_2$)$_n$CON(R$_1$)CH(R$_2$)COOCH$_3$     Formula XVI wherein n, R$_1$ and R$_2$ are as defined in Formula I and R$_c$ is p-nitrophenyl, in a polar aprotic solvent such as dimethylformamide or dimethylsulfoxide at 40° to 50° C. in the presence of one equivalent of a tertiary amine such as pyridine and a catalytic amount of dimethylaminopyridine or N-methylimidazole and subsequently hydrolyzing the thus formed methyl ester derivative to the corresponding free acid using aqueous acid. The Formula XVI compounds are prepared by treating a lactone of Formula XV with a methyl ester of an appropriate amino acid as identified above in a polar aprotic solvent in the presence of one equivalent of a non-nucleophilic base at elevated temperature to give compounds of the formula HO(CH$_2$)$_n$CON(R$_1$)CH(R$_2$)COOCH$_3$ which are treated with a slight excess of p-nitrophenylchlorocarbonate in a dry aprotic solvent at 0° to 20° C. in the presence of a stoichiometric amount of pyridine or a tertiary amine.

The salts of the compounds of Formula I are prepared by treating the acid with a suitable base as generally described hereinabove.

EXAMPLE 1

(a) Preparation of 6-(carboxymethylthio)hexanoate

Seven ml of mercaptoacetic acid was dissolved in 310 ml of 1N NaOH and 19.5 g of 5-bromocaproic acid was added. The solution was stirred for 16 hours after which it was combined with 160 ml of 2N HCl. The acidified solution was extracted three times with ethyl acetate and the combined extracts were concentrated to about 40 ml. The concentrate was then diluted with about 100 ml ether and 200 ml hexane. A white solid formed which was collected by filtration (yield, 19.1 g; m.p., 85°–86° C.).

(b) Preparation of 6-(carboxymethylsulfonyl)hexanoate 6.2 g of the sulfide of Example 1(a) was stirred with a mixture of 40 ml glacial acetic acid and 40 ml 30% hydrogen peroxide at room temperature for about 16 hours and at 50° C. for two hours. Stirring with a pinch of palladium on charcoal removed much of the excess peroxide. The remaining peroxide was eliminated by adding aqueous sodium thiosulfate until it was all reduced. The solution was then diluted with water and extracted several times with ethyl acetate. The pooled extracts were concentrated to dryness and the residue was taken up in hot ethyl acetate. Upon cooling and filtering 4.2 g of white crystalline solid was obtained (m.p., 155°–157° C.).

(c) Preparation of methylprednisolone, 21-[6'-(carboxymethylsulfonyl)hexanoate]

143 g of the compound of Example 1(b) was dissolved in 25 ml dry DMF along with 2.42 g of methylprednisolone-21-iodide. This solution was then treated with 1.80 ml of DBU (1,8-diazabicyclo[5.4.0]undec-7-ene) and was stirred for two hours at room temperature. The reaction mixture was then diluted to 200 ml with ethyl acetate and washed with two 100 ml portions of 0.1N HCl. The organic phase was further washed with a dilute sodium thiosulfate solution to remove traces of iodine. The colorless organic phase was then extracted with 100 ml of dilute sodium bicarbonate solution and the separated aqueous phase was quickly acidified. This aqueous solution was then extracted with ethyl acetate, the extract was dried over sodium sulfate, and the dried solution was concentrated to a glassy solid. The solid was recrystallized from propionitrile. 1.3 g of a white crystalline solid was obtained.

Elemental analysis calculated for $C_{30}H_{42}SO_{10}$: C, 60.59; H, 7.12; S, 5.29. Found (corrected for water): C, 60.70; H, 7.17; S, 5.23.

Water: 0.06%. Melting point: 184°–185° C.

UV (MeOH): $A_{max}$ at 243 nm, $E_{243} = 1.48 \times 10^4$ (methylprednisolone $E_{243} = 1.46 \times 10^4$).

EXAMPLE 2

(a) Preparation of 6-(carboxymethylsulfinyl)hexanoic acid

A chilled solution of 4.12 g of the 6-(carboxymethylthio)hexanoic acid of Example 1(a) in 130 ml MeOH was mixed with a chilled solution of 4.28 g sodium meta-periodate in 320 ml water. The mixture was maintained at about 5° C. for two days, after which it was diluted with two volumes of cold acetonitrile. Solid sodium iodate was removed by filtration and the filtrate was concentrated to an oily residue under reduced pressure. The oil was characterized by NMR and was not further purified. NMR (in Unisol-D): 10.2–10.5 (S, 2, COOH), 3.6–3.8 (S, 2, S(O)—CH₂—COOH), 2.7–3.1 (M, 2, —CH₂—S(O), 2.1–2.5 (M, 2, —CH₂—COOH), 1.4–1.9 (M, 6, —CH₂—) (also a small peak at=4.0 indicating some sulfone present).

(b) Preparation of methylprednisolone-21-[6'-(carboxymethylsulfinyl)hexanoate]

2.7 g of the crude sulfoxide of Example 2(a) was added to a solution of 3.8 g of the 21-iodo derivative of methylprednisolone and 8.3 g of diisopropylethylamine in 40 ml of DMF and the resulting solution was stirred for about 16 hours at room temperature. The reaction mixture was then concentrated under reduced pressure and partitioned between ethyl acetate and dilute HCl. The ethyl acetate phase was extracted with a phosphate buffer solution at pH 6.4, after which this aqueous extract was acidified and re-extracted with ethyl acetate. The ethyl acetate solution, now enriched in the desired compound, was concentrated to an oil. Final isolation was accomplished by preparative reversed phase chromatography. Pooled fractions containing the desired product were concentrated, dissolved in 5 ml methanol, and dripped slowly into 200 ml of ethyl ether with stirring. A white semi-crystalline solid formed which was isolated by filtration. Yield, 600 mg.

Elemental analysis calculated for $C_{30}H_{42}SO_9$: C, 62.26; H, 7.32; S, 5.54. Found (corrected for water): C, 62.46; H, 7.28; S, 5.42.

Water: 0.38%. Melting point: 166°–170° C.

EXAMPLE 3

(a) 6-(Carboxymethylthio)-1-hexanol 4.5 ml (0.04M) of 6-chloro-1-hexanol is added to a solution of 2.8 ml (0.04M) of mercaptoacetic acid in 120 ml of 1N NaOH. The solution is warmed to about 50° C. for 16 hours, then acidified and extracted repeatedly with ethyl acetate. The combined extracts are concentrated to dryness and the residue purified by recrystallization.

(b) 6-(Carboxymethylsulfonyl)-1-hexanol

The compound of Example 3(a) is dissolved in 30 ml glacial acetic acid to which 30 ml of 30% $H_2O_2$ is added. After stirring one day at room temperature, the reaction mixture is diluted with an aqueous solution of sodium thiosulfate and extracted repeatedly with ethyl acetate. It is necessary to use enough sodium thiosulfate to reduce all residual peroxides. The pooled ethyl acetate extracts are then concentrated to a solid residue which is purified by recrystallization.

(c) 6-(Carboxymethylsulfonyl)-1-hexanol, methyl ester

The compound of Example 3(b) is refluxed for 16 hours in 100 ml methanol containing 0.5 ml of concentrated $H_2SO_4$. The product is isolated by removing most of the methanol under reduced pressure, diluting with ethyl acetate, and washing with water. The ethyl acetate is then removed under reduced pressure.

(d) p-Nitrophenylcarbonate ester of Example 3(c)

4.8 g (0.02M) of the compound of Example 3(c) is treated with 4.2 g (0.021M) of p-nitrophenylchlorocarbonate and 2.9 ml of triethylamine in dry THF at room temperature. After stirring several hours, the triethylammonium hydrochloride is filtered off and the filtrate is concentrated to dryness. The residue is purified by crystallization and/or chromatography on silica gel.

(e) Hydrocortisone-21-carbonate ester of Example 3(c)

4 g (0.01M) of the compound of Example 3(d) and 2.9 g (0.008M) of hydrocortisone are dissolved in 30 ml dry DMF and treated with 1.2 g of dimethylaminopyridine. The reaction mixture is stirred at 50° C. for one day. After this time the reaction mixture is diluted with water and the resulting solution maintained at pH 7 in the presence of a catalytic amount of imidazole until all excess p-nitrophenylcarbonate is selectively hydrolyzed. The mixture is then partitioned between ethyl acetate and water at pH 7. The organic extract is concentrated, and the residue is retained for the next step.

(f) Hydrocortisone-21-[6'-(carboxymethylsulfonyl)-1'-hexanol]-carbonate

The residue from Example 3(e) is taken up in aqueous DMF and treated with sufficient HCl to lower the pH to around 1. The reaction is monitored carefully and stopped after most of the methyl ester has been selectively cleaved. The pH is then adjusted to 7 and the mixture is partitioned between water and ethyl acetate. The aqueous phase is separated, acidified, and extracted with ethyl acetate. The ethyl acetate extract is then concentrated under reduced pressure and the residue is purified by chromatography and/or crystallization.

EXAMPLE 4

| | |
|---|---|
| Methylprednisolone,21-[6-(carboxymethylsulfonyl)-hexanoate] | 155 mg |
| Dilute NaOH to adjust pH to 5.3 | |
| Sterile water for injection to make 1 mlr | |

EXAMPLE 5

| | |
|---|---|
| Methylprednisolone,21-[6-(carboxymethylsulfonyl)-hexanoate] | 153 |
| Adipic acid | 7.3 mg |
| Methyl paraben | 0.2 mg |
| Propyl paraben | 0.2 mg |
| NaOH (dilute) to adjust pH to 5.4 | |
| Sterile water for injection to make 1 ml | |

EXAMPLE 6

| | |
|---|---|
| Methylprednisoline,21-[6-(carboxymethylsulfonyl)-hexanoate] | 166 |
| Creatine | 8.0 mg |
| Acetic acid | 4.6 mg |
| Sodium acetate | 2.0 mg |
| Sodium bisulfite | 1.0 mg |
| Disodium edetate | 0.5 mg |
| Benzyl alcohol | 8.8 mg |
| HCl (dilute) or NaOH (dilute) to adjust pH to 5.0 | |
| Water for injection to make 1 ml | |

EXAMPLE 7

(a) Preparation of trialkyl 2-oxalyl adipate

Carefully dried absolute ethanol (32 mls) was distilled directly into a 3-neck flask with reflux condenser and dry nitrogen line. 2.07 g (0.09M) of sodium metal was added and the mixture was stirred while refluxing until all sodium had dissolved. Unreacted ethanol was then removed by distillation, driving off the last traces by adding dry toluene and continuing the distillation. The pasty mass of sodium ethoxide was then cooled and suspended in 60 mls anhydrous ethylether. Diethyl oxylate (13.15 g) was then added followed by dimethyl adipate (15.7 g). The reaction mixture was stirred briefly then allowed to stand at room temperature for twelve hours. After this time the ether solution was extracted with 80 mls water and the ether phase was washed with 40 more mls water. The combined aqueous phases were acidified to pH 1 with conc HCl whereupon the product oiled out of solution. The oil was extracted out with ether and the ether solution was dried over $Na_2SO_4$. After removing the ether under reduced pressure 15.0 g of yellow oil was obtained.

(b) Preparation of 2-oxo-heptanedicarboxylic acid

The compound of Example 7(a) (15 g) was heated with 70 mls of 4N HCl to 65° C. for 10 hrs. The water and HCl were removed under reduced pressure to give a yellow oil which solidified on standing at room temperature. The solid was taken up in minimal acetone and diluted to 200 mls with chloroform. A small amount of oxalic acid impurity crystallized out. The solution was then diluted with hexane resulting in the precipitation of 4.8 g of the desired product as a yellowish solid.

Melting point: 88°–91° C.

Proton NMR: $\delta 1.5$–1.8 (m, 4), $\delta 2.1$–2.5 (m, 2), $\delta 2.7$–3.0 (m, 2), $\delta 11.9$ (broad s, 2).

IR (Nujol mull): 3400–2000 (very broad); 1700 (strong, broad); 1260 (average); 1203 (sharp), 1091, 1061, 1016 (sharp); 880 (broad).

(c) Preparation of methylprednisolone,21-(6'-oxo-heptanedicarboxylate)

1.74 g (0.01M) at 2-oxoheptanedicarboxylic acid was dissolved in 30 mls of DMF and 3 mls (0.02M) of DBU was added. To this solution was added 3.88 g of methylprednisolone-21-iodide and the mixture was stirred for about 14 hours. The rxn mixture was then partitioned between 200 mls each of ethylacetate and 0.1N HCl. The organic phase was retained and washed with more dilute acid. The organic phase was then extracted with water adjusted to pH 7. The aqueous extract was separated, acidified to pH 3, and extracted with ethyl acetate. The ethylacetate extract was dried over sodium sulfate and concentrated to an oil. Trituration of the oil with diethyl ether gave a white solid.

Yield 2.55 g.

Melting point: 161.5°–165° C.

Proton NMR: $\delta 0.6$–3.0 (overlapping multiplets, 25); $\delta 0.9$ (s, 3); $\delta 1.5$ (s,3); $\delta 4.3$–4.6 (m, 1); $\delta 4.65$–5.35 (m, 2); $\delta 5.95$ (broad s, 1); $\delta 6.05$–6.35 (m, 1); $\delta 7.25$–7.5 (d, 1).

IR (Nujol mull): 3570, 3535, 3450 (average); 3300–2000 (very broad); 1750, 1735, 1720 (strong, average), 1645 (sharp), 1590, 1565 (average); 1202 (average); 1040, 915, 890 (sharp).

FORMULA CHART

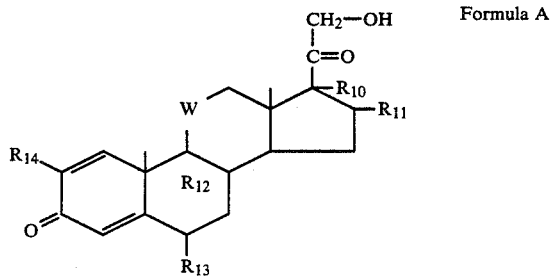

Formula A

In the above Formula A:

ω is

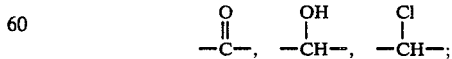

$R_{10}$ is H, α-OH;
$R_{11}$ is H, α-$CH_3$, β-$CH_3$, α-F, β-F, α-OH or =$CH_2$;
$R_{12}$ is H, F, Cl, Br;
$R_{13}$ is H, α-F, α-$CH_3$, β-$CH_3$, α-Cl, β-Cl, β-OH;
$R_{14}$ is H, $CH_3$.

-continued
FORMULA CHART

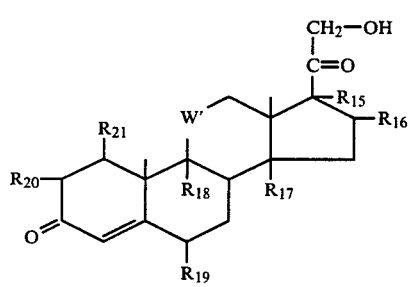

Formula B

In the above Formula B:
W' is

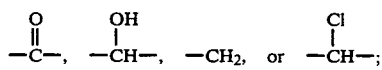

$R_{15}$ is H, α-OH, α-CH$_3$;
$R_{16}$ is H, α-OH, α-CH$_3$;
$R_{17}$ is H, α-OH;
$R_{18}$ is H, α-F, β-F, α-Br, α-Cl, α-OH;
$R_{19}$ is H, β-OH, α-CH$_3$, β-CH$_3$, α-F, α-Cl,
$R_{20}$ is H, α-F, Cl, α-CH$_3$, =CH$_2$;
$R_{21}$ is H, α-OH; with the proviso that one of $R_{20}$ and $R_{21}$ is hydrogen; preferably $R_{17}$, $R_{20}$ and $R_{21}$ are hydrogen.

We claim:
1. A compound of the formula

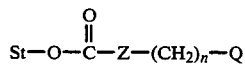

wherein
St represents a corticosteroid moiety bonded to the carbonyl via the 21-hydroxy group of said corticosteroid;
wherein
Z is a bond or —O—;
wherein
n is an integer from 4 to 9;
wherein
Q is
(1) Y—CH$_2$COOH wherein Y is —S—, —S(O)—, —S(O$_2$)—, —SO$_2$N(R)—, or —N(R)SO$_2$; R is hydrogen or lower alkyl(C$_1$-C$_4$) with the proviso that the total carbon atoms in R and (CH$_2$)$_n$ is not greater than 10;
(2)

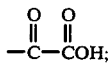

or
(3)

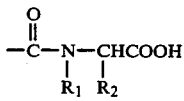

wherein
$R_1$ is hydrogen and $R_2$ is H, CH$_3$, CH$_2$COOH, CH$_2$CH$_2$COOH, CH$_2$OH, CH$_2$SH, CH$_2$CH$_2$SCH$_3$, or CH$_2$Ph—(OH) wherein Ph is phenyl and Ph—(OH) is p-hydroxyphenyl; or $R_1$ is CH$_3$ and $R_2$ is H; or $R_1$ and $R_2$ taken together are —CH$_2$CH$_2$CH$_2$—; or N(R$_1$)CH(R$_2$)COOH taken together is NHCH$_2$CONHCH$_2$COOH; and pharmaceutically acceptable salts thereof.
2. A compound of claim 1 wherein Q is YCH$_2$COOM.
3. A compound of claim 2 wherein Z is a bond.
4. A compound of claim 3 which is methylprednisolone,21-[6-(carboxymethylsulfinyl)hexanoate].
5. A compound of claim 3 which is methylprednisolone,21-[6-(carboxymethylsulfonyl)hexanoate].
6. A compound of claim 1 wherein Q is

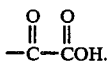

7. A compound of claim 6 wherein Z is a bond.
8. A compound of claim 7 which is methylprednisolone,21-('-oxo-heptanedicarboxylate).
9. A compound of claim 1 wherein the corticosteroid forming the St moiety is 6α-methylprednisolone, hydrocortisone, corticosterone, prednisone, prednisolone, triamcinolone, dexamethasone, betamethasone, flumethasone, 11-deoxycorticosterone, fluprednisolone, 9α-fluorohydrocortisone, paramethasone, chlorprednisone or dehydrocorticosterone.
10. A pharmaceutical composition comprising an effective quantity of a compound of claim 1 as a sterile aqueous solution.
11. A composition of claim 10 which is in unit dosage form.
12. A composition of claim 11 wherein the compound is:
methylprednisolone,21-[6-(carboxymethylsulfinyl)-hexanoate],
methylprednisolone,21-[6-(carboxymethylsulfonyl)-hexanoate].

* * * * *

UNITED STATES PATENT OFFICE
CERTIFICATE OF CORRECTION

Patent No. 4,588,718    Dated   May 13, 1986

Inventor(s)   Bradley D. Anderson and Robert A. Conradi

It is certified that error appears in the above-identified patent and that said Letters Patent are hereby corrected as shown below:

Front page, column 2, line 4: "Derivaties" should read -- Derivatives --.

Column 3, line 55: "2735; 2746;" should read -- 2735; 2736; --.

Column 15, line 19: "0.2 mg" should read -- 1.5 mg --.

Column 16, line 50, Formula Chart: 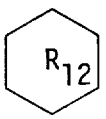 should read -- 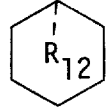 --.

Column 18, line 37, Claim 8: "( '-oxo-" should read -- (6'-oxo- --.

Signed and Sealed this
Twenty-fifth Day of November, 1986

*Attest:*

DONALD J. QUIGG

*Attesting Officer*    *Commissioner of Patents and Trademarks*